US005474909A

United States Patent [19]
Connors et al.

[11] Patent Number: 5,474,909
[45] Date of Patent: Dec. 12, 1995

[54] NONCOLORIMETRIC HISTOCULTURE METHOD FOR PREDICTING DRUG RESPONSE OF TUMORS

[75] Inventors: Kenneth M. Connors; Hui-Yan Guo, both of San Diego, Calif.

[73] Assignee: Anticancer, Inc., San Diego, Calif.

[21] Appl. No.: 926,681

[22] Filed: Aug. 7, 1992

[51] Int. Cl.$^6$ .............................. C12Q 1/02; C12Q 1/00; C12N 5/00; G01N 33/48

[52] U.S. Cl. .............................. 435/29; 435/4; 435/7.21; 435/70.3; 435/240.2; 435/240.23; 435/960; 435/7.23; 435/32; 436/63

[58] Field of Search .................................. 435/21, 29, 4, 435/7.21, 70.3, 240.2, 240.23, 960, 7.23, 32; 436/63, 501, 805; 530/370, 387; 549/454, 341

[56] References Cited

U.S. PATENT DOCUMENTS 4,345,027 8/1982 Dolbeare .................................. 436/63
5,055,556 10/1991 Stryer et al. ............................. 436/501

OTHER PUBLICATIONS

Colangelo et al, Analytical Biochemistry, vol. 205 (1), pp. 8–13, 1992.
Ross et al, Cancer Research, vol. 49, pp. 3776–3782, 1989.
Reile et al, Analytical Biochemistry, vol. 187, pp. 262–267, 1990.
Suto et al, Journal of Surgical Oncology 42:28–32 (1989).
Ford et al, Cancer Chemother Pharmacol (1989) 24:295–301.
Vescio et al, Proc. Natl. Acad. Sci. USA (1991) vol. 88, pp. 5163–5166.
Alley et al, Cancer Research 51, 1247–1256, Feb. 15, 1991.
Kern et al, "Highly Specific Prediction of Antineoplastic Drug Resistance With an In Vitro Assay Using Supraphar-macologic Drug Exposures," *J. Natl. Cancer Inst.*, 82:582–588 (1990).
Weisenthal et al, "Comparison of Dye Exclusion Assays with a Clonogenic Assay in the Determination of Drug–induced Cytotoxicity," *Cancer Res.*, 43:258–264 (1983).
Vescio et al, "In Vivo–Like Drug Responses of Human Tumors Growing in Three–Dimensional Gel–Supported Primary Culture," *Proc. Natl. Acad. Sci. USA,* 84:5029–5033 (1987).
Hoffman et al, "A General Native–State Method for Determination of Proliferation Capacity of Human Normal and Tumor Tissues In Vitro," *Proc. Natl. Acad. Sci. USA,* 86:2013–2017 (1989).
Ford et al, "Comparison of Tetrazolium Colorimetric and [$^3$H]–Uridine Assays for In Vitro Chemosensitivity Testing," *Cancer Chem. Pharmacol.,* 24:295–301 (1989).
Suto et al, "MTT Assay with Reference to the Clinical Effect of Chemotherapy," 42: 28–32 (1989).
Furukawa et al, "High In Vitro–In Vivo Correlation of Drug Response Using Sponge–Gel–Supported Three Dimensional Histoculture and the MTT End Point," *Int. J. Cancer,* 51:489–498 (1992).
Freeman et al, "In Vivo–Like Growth of Human Tumors in Vitro," *Proc. Natl. Acad. Sci. USA,* 83:2694–2698 (1986).
Vescio et al, "Correlation of Histology and Drug Response of Human Tumors Grown in Native–State Three–Dimensional Histoculture and in Nude Mice," *Proc. Natl. Acad. Sci. USA,* 88:5163–5166 (1991).
Hoffman et al, "In Vivo–Like Growth of Human Tumors In Vitro," *Proc. Natl. Acad. Sci. USA,* 83:2694–2698 (1986).

*Primary Examiner*—William H. Beisner
*Assistant Examiner*—Louise N. Leary
*Attorney, Agent, or Firm*—Thomas Fitting

[57] ABSTRACT

A method of evaluating the effectiveness of drugs in inhibiting the growth of tumor cells. A sample of a tumor is histocultured, a drug to be evaluated is added to the sample and the sample is incubated. A suitable tetrazolium salt is added and a frozen section of the sample is prepared. The section is stained with a fluorescent dye. The section is exposed to polarized light and the reflected light is measured. Then the section is exposed to fluorescent light and the light emitted by the dye is measured. These measurements are compared to a control and/or measurements from tests using other drugs and the relative effectiveness of the drug is evaluated, preferably by pixel analysis.

24 Claims, 5 Drawing Sheets

|  | MITOMYCIN C | DOXORUBICIN | 5-Fu | CISPLATINUM | MELPHALAN |
|---|---|---|---|---|---|
| TRUE POSITIVE | 3 | 0 | 2 | 1 | 1 |
| TRUE NEGATIVE | 2 | 6 | 6 | 5 | 5 |
| FALSE POSITIVE | 0 | 1 | 0 | 1 | 0 |
| FALSE NEGATIVE | 4 | 1 | 1 | 2 | 1 |
| ACCURACY | 0.56 | 0.75 | 0.89 | 0.67 | 0.86 |
| SPECIFICITY | 1 | 0.86 | 1 | 0.83 | 1 |
| PREDICT. POS. VAL. | 1 | 0 | 1 | 0.50 | 1 |
| PREDICT. NEG. VAL. | 0.33 | 0.86 | 0.86 | 0.71 | 0.83 |

TOTAL ACCURACY OF THE ASSAY = 74.6%
TOTAL SPECIFICITY " " = 93.8%
TOTAL PREDICT. POS. VAL." = 70.0%
TOTAL PREDICT. NEG. VAL." = 71.8%

FIG. 13

NONCOLORIMETRIC HISTOCULTURE METHOD FOR PREDICTING DRUG RESPONSE OF TUMORS

TECHNICAL FIELD

The present invention relates in general to an in vitro test to accurately predict cancer-patient response to chemotherapy and, more particularly, to a noncolorimetric method of measuring tumor metabolic activity in response to selected drugs.

BACKGROUND OF THE INVENTION

Often, in the treatment of cancer through chemotherapy, different patient's tumors respond differently to different drugs. The ability to accurately predict the response of a specific patient to each of the drugs that might be used would greatly aid treatment.

The clonogenic assay, as described by Puck et al., *J. Exp. Med.*, 103:653–666 (1956) and applied by Hamburger et al., *Science*, 197:461–463(1977), was developed in the late 1970s and became widely used for in vitro drug response assays for tumor cells. It is based on the ability of disaggregated tumor cells to grow in an agar or agar-like medium and form colonies. That assay correlates relatively well with clinical drug resistance but has several problems, such as the small percentage of tumors that can be evaluated, poor predictivity of clinical drug sensitivity and clump artifacts. Also, this technique requires a very long time to supply useful data and has difficulty in testing multiple drugs which detract from the usefulness of that assay.

Modifications of the clonogenic assay have been developed [for example the Kern and Weisenthal thymidine-incorporation clonogenic assay, Kern et al., *J. Natl. Cancer Inst.* 82:582–588 (1990) and the suspension-cell dye-incorporation assay, Weisenthal et al., *Cancer Res.*, 43:258–264 (1983)]. However, these assays show a less than desirable prediction of clinical drug sensitivity and a low evaluation rate for solid tumors. In addition, all of these assays are artifactual in that they involve separating single cells from the original tissue.

Short term assays, such as are described by Sanfilppo et al., *Eur. Urol.*, 16:450–455 (1989), in which tumor fragments and tritiated nucleic acids are used, show some good clinical correlations but limit the viability of the tumors, which basically limits their use to the institution from which the tumors are derived.

Recently, as described by Vescio et al., *Proc. Natl. Acad. Sci. USA*, 84:5029–5033 (1987), an assay using a three-dimensional human-tumor sponge-gel-supported histoculture system with a [$^3$H]thymidine-incorporation endpoint has been developed, based on the earlier development of sponge-gel culture by Leighton as described in *J. Natl. Cancer Inst.*, 12:545–561 (1951) and 15:275–293 (1954). This histoculture system allows tumor fragments to grow while maintaining many of their in vivo properties, including tissue architecture [Hoffman et al., *Proc. Natl. Acad. Sci. USA*, 86:2013–2017 (1989)]. Using histoculture with [$^3$H] thymidine incorporation measured by histological autoradiography, in vivo drug resistance can be accurately predicted. However, while in vivo drug response, or chemosensitivity, is accurately predicted for some drugs it is not for others.

Using the MTT end point as described by Ford et al., *Cancer Chem. Pharmacol.* 24:295–301 (1989) on cells in suspension, relatively high in vitro-in vivo correlations have been observed, Suto et al., *J. Surg. Oncol.*, 42:28–32 (1989). The application of the MTT end point to the histoculture assay has been found (Furukawa et al., *Int. J. Cancer,* 51:489–498 (1992)) to increase the overall in vitro-in vivo correlative ability of the assay. However, formazan crystal formation from MTT due to succinate dehydrogenase activity is measured in this method by spectrophotometric methods after extraction, which does not allow simultaneous histological observation, does not correct for tumor heterogeneity and is labor intensive.

Thus, there is a continuing need for in vitro assays that accurately and rapidly predict in vivo drug response for a wide variety of drugs and permit observation of the variable drug response in a well maintained histoculture to take into account the heterogeneity present in the tumor with regard to drug response.

BRIEF SUMMARY OF THE INVENTION

It is, therefore, an object of this invention to provide an assay system overcoming the above-noted problems. Another object is to provide an in vitro test method that rapidly and accurately predicts cancer-patient response to chemotherapy. A further object is to provide an in vitro test using histocultured tumor pieces rather than single cells. Yet another object is to provide an in vitro test that can rapidly compare the response of tumors to several drugs in parallel with high correlation of the in vivo effect of those drugs.

The above-noted objects, and others are accomplished in accordance with this invention by a method that, basically, comprises steps of providing a sample of gel-supported, three-dimensional histocultured pieces of tumor tissue, adding a quantity of a selected drug to the tissue and histoculturing the tissues, removing the drug from the histoculture, adding a quantity of a suitable tetrazolium salt to the sample, preferably MTT, and histoculturing the tissue, preparing frozen sections of the sample, staining the section with a suitable fluorescent dye to visualize the cells, preferably propidium iodide, and finally analyzing the samples.

The sample can be examined through a microscope using polarized light, with areas of reflected brightness observable corresponding to the amount of formazan crystals which is indicative of remaining living cells. This also permits the observation of the relative effect of the tested drug on different areas of heterogeneous tumors. The sample can also be observed through the microscope using suitable light excitation filtration to produce fluorescence proportional to the number of cells present after staining the frozen section of the tumor with propidium iodide or other fluorescent dyes of this invention. Thus, the areas of a tumor which respond to the drug can be easily determined and evaluated.

The samples can be analyzed by pixel image analysis, first using polarized light to determine a figure for formazan crystals present that result from the tetrazolium salt reduction and second under fluorescent light to obtain a figure for the propidium iodide. Similar control tests and pixel image analyses are run on a tissue sample that had not been treated with a drug.

For optimum results, 3-(4,5-dimethylthiazol-2-yl)-2,5-diphenyltetrazolium bromide (MTT) is the preferred tetrazolium salt and propidium iodide is the preferred fluorescent dye.

The sensitivity of the tumor to the drug can be determined by using the formula:

Inhibition rate=100−[(PIAFC$_{Treated}$/PIAFD$_{Treated}$)/(PIAFC$_{Control}$/PIAFD$_{Control}$)×100], where PIAFC is pixel image analysis of formazan crystal reflection and PIAFD is pixel image analysis of the fluorescent dye emissions.

BRIEF DESCRIPTION OF THE DRAWING

Details of the invention, and of certain preferred embodiments thereof, will be further understood upon reference to the drawing, wherein:

FIG. 13 is a table showing a summary of the correlative drug responses results obtained from the comparison between the in vitro non-colorimetric MTT end point and the in vivo xenograft results as described in Example X. In vitro drug response sensitivity was scored when a drug produced a reduction of 60% or lower compared to the control, when calculated by pixel analysis as described herein. In vivo drug response sensitivity was scored when the relative mean tumor weight was 42% or less of the control relative mean tumor weight as described in Example X after exposure to the drug.

DETAILED DESCRIPTION OF PREFERRED EMBODIMENTS

Figure 1:
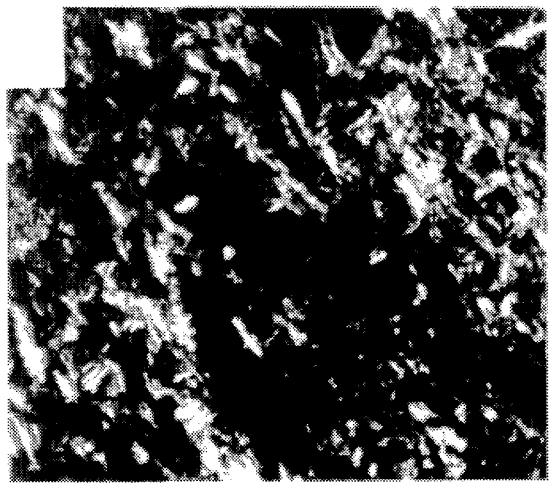
FIG. 1 is a photomicrograph of the tumor sample incubated with an ineffective drug under polarized light, showing the appearance of the formazan crystals indicative of viable cells.

This invention provides a method making possible the rapid and accurate determination of the relative efficacy of antineoplastic drugs with respect to specific tumors for specific patients. A plurality of samples of the same tissue can be simultaneously histocultured in a plurality of culture containers, typically the wells of a multi-well culture plate. Each sample may be treated with different drugs, different dose rates and different combinations of drugs. The relative effectiveness of the drug samples can be directly compared. A high correlation between the results of the in vitro tests to corresponding in vivo tests has been achieved. Further, the relative efficacy of the drug across different areas of a three-dimensional heterogeneous tumor histoculture can be evaluated.

The method of this invention may be applied to any suitable tissue, both normal tissues and primary or metastatic tumors, including solid tumors (both carcinomas and sarcomas) and the like. Typical types of carcinomas (adeno, squamous and undifferentiated variants for carcinomas of different sites) to which the present invention is applicable include adrenal, bladder, breast, colon, kidney, lung, ovary, pancreas, prostate, thyroid, upper airways (head and neck), uterous (corpus and cervix), bile ducts, choriocarcinoma, esophagus, liver, parathyroid, rectum, salivary glands, small bowel, stomach, testis, tongue and urethra. Typical types of sarcomas and other neoplasms to which the method of this invention are applicable include diffuse lymphomas, Ewing's sarcoma, Hodgkin's disease, melanoma (melanotic and amelanotic), multiple myeloma, nephroblastoma (Wilm's tumor), neuroblastoma, nodular lymphomas, rhabdomyosarcoma, angiosarcoma, brain tumors (gliomas), chondrosarcoma, dysgerminoma, fibrosarcoma, leiomyosarcoma, liposarcoma, medulloblastoma, mesothelioma, osteosarcoma, retinoblastoma and thymoma.

Tumor specimens are typically explanted for histoculture by an aseptic surgical procedure and minced aseptically into about 0.5 to 1.0 mm$^3$ pieces. Best results are obtained with approximately cubical 1 mm$^3$ pieces. Preferably, multiple portions of a tumor are examined in parallel culture assays because of the heterogeneous nature of most tumors. As discussed above, the method of this invention permits the heterogeneity of the tumor to be taken into account.

Any suitable method may be used for culturing the tumors, so long as the three dimensional architecture of the tissue to be evaluated is maintained. Culturing of intact tissue to preserve the three dimensional architecture is referred to as histoculture. Typical histoculturing methods include those described by Freeman et al., *Proc. Natl. Acad. Sci. USA*, 83:2694–2698, 1986; Vescio eta ., *Proc. Natl. Acad. Sci. USA*, 84:5029–5033, 1987; Hoffman et al., *Proc. Natl. Acad. Sci. USA*, 86:2013–2017, 1989; and Vescio et al., *Proc. Natl. Acad. Sci. USA*, 88:5163–5166, 1991, (these references, and others cited herein, are hereby incorporated by reference in this application). The tumor pieces to be cultured are placed on a suitable support material in one or more separate containers or wells. The support material may be any suitable material having a trabecular structure with interstices capable of delivering aqueous nutrients from a liquid medium in contact with the support material by capillary action to the tumor pieces. The support material may be a suitable mesh formed from a synthetic resin such as nylon, borosilicate glass fiber, polypropylene or a natural organic material such as cellulose or collagen. Preferred materials include gelatinized pig skin, a collagen-containing gel termed "Spongestan" available from Health Designs, Inc. (Rochester, N.Y.) or the Upjohn Company (Kalamazoo, Mich.) under the Gelfoam trademark, a homopolysaccharide sponge of the sort described by Leighton, *J. Natl. Cancer Inst.* 12:545–561 (1951) and combinations of collagen-containing gels and homopolysaccharide sponge materials.

A suitable quantity of a liquid culture nutrient media capable of supporting tissue cell growth is placed in each well in contact with the support material but not covering the tumor specimens. Eagle's minimal essential medium (MEM), (described by Eagle, *Science*, 122:501, 1955, and Eagle, *Science*, 130:432, 1959) is a preferred culture medium.

The histoculture samples are then incubated for a suitable period up to about 1 to 4 days, and preferably about 12 to 48 hours in a high humidity environment at a temperature approximately corresponding to the body temperature of the animal from which the tumor samples were derived (about 37° C. for human tissue).

The samples are then treated with suitable antitumor drugs by admixture of preselected amounts of the drug to the histoculture medium. Different drugs, mixtures of drugs and various dosages may be used, as desired, for comparison purposes. Generally, the drugs are used at concentrations corresponding to the levels achievable clinically. The drugs are dissolved in any suitable agent, typically saline solution or ethanol to facilitate their addition to the histoculture. Tests may be made with drugs of known antitumor capability and other agents of unknown capability. Typical known antitumor drugs include mitomycin-C, doxorubicin, 5-fluorouracil, cisplatin, melphalan, carmustine, vinblastine, vincristine and bleomycin, all of which are available from the Sigma Chemical Co.

Preferably, the tissue samples are again incubated with the drug as described above for a suitable period, typically about 12 to 48 hours and preferably about 24 hours. The drug is then removed from the sample, preferably by washing the tissue sample in fresh, drug-free medium to remove residual drug from the histoculture.

A suitable tetrazolium salt solution is prepared by dissolving the selected salt in a suitable stock solution such as saline, which is preferably phosphate-buffered. Typical tetrazolium salts include 3-[4,5-Dimethylthiazol-2-yl] -2,5-diphenyltetrazolium bromide (MTT), 2,2',5,5'-Tetra-p-nitrophenyl- 3,3'-[3,3'-dimethoxy-4,4'-diphenylene] ditetrazolium chloride (TNBT), 3,3'-[3,3'-Dimethoxy( 1,1'-bi-phenyl)-4,4'-diyl]-bis[2,5'-diphenyl-2H-tetrazolium] dichloride (tetrazolium blue; TB), 2,3,5-Triphenyltetrazolium chloride (tetrazolium red; TR), 2,5-Diphenyl- 3-[α-naphthyl]-tetrazolium chloride (tetrazolium violet; TV), 2-[4-Iodophenyl]-3-[4-nitrophenyl]-5-phenyltetrazolium chloride (INT), 2,2',5,5'-Tetraphenyl- 3,3'-[p-diphenylene] ditetrazolium chloride, 2,2'-Di-p-nitrophenyl- 5,5'-diphenyl-3,3'-[3,3'-dimethoxy-4,4'-diphenylene] ditretrazolium chloride (NBT), 2,2'-Di[p-nitrophenyl] -5,5'-di[p-thiocarbamylphenyl]-3,3'-[3,3'-dimethoxy- 4,4'-biphenylene]ditretrazolium chloride (TC-NBT), and mixtures thereof.

The selected tetrazolium salt, preferably MTT, is dissolved in a suitable medium, typically phosphate-buffered saline (PBS). The preferred concentration is from about 4 mg/ml to 12 mg/ml, with optimum results at about 8 mg/ml. The solution is preferably filtered before use. From about 50 to 200 µl of the MTT solution is added to each sample cell. Best results are obtained with about 100 µl. The samples are preferably again incubated for at least 1 to about 3 hours under incubation conditions as described above.

The samples are then removed, frozen, and frozen sections of about 4µ are made in a conventional manner. The resulting slides are dipped in a suitable fluorescent dye solution for from about 30 seconds to 2 minutes to allow the stain to penetrate the section and stain the cells in the section, providing a detectable indication of the number of cells in the section, dead or alive. A 1 minute dip is preferred. Typical suitable stains for labelling cells are any stain that is specific for cells and which is detectable by light microscopy. Preferred are the family of fluorescent dyes that intercalate DNA and thereby fluoresce, indicating the presence of nuclei. Such dyes are generally known as high-affinity nucleic acid stains. Exemplary fluorescent dyes are ethidium bromide (EtBr), ethidium homodimer, propidium iodide (PI), and the like dyes including the derivatives BOBO-1 iodide, BOBO-3 iodide, BO-PRO- 1 iodide, BO-PRO-3 iodide, POPO-1 iodide, POPO-3 iodide, PO-PRO-1 iodide, PO-PRO-3 iodide, TOTO-1 iodide, TOTO-3 iodide, TO-PRO-1 iodide, TO-PRO-3 iodide, YOYO-1 iodide, YOYO-3 iodide, YO-PRO-1 iodide, and YO-PRO-3 iodide available from Molecular Probes, Inc., (Eugene, Oreg.). Particularly preferred is PI, and is utilized as exemplary herein. In each case where a different stain is used, a filter system is selected to produce light of wavelengths to which the fluorescent dye is sensitive. Excellent results are obtained using these dyes.

The slides are then dried and examined with a microscope, typically at about 200× utilizing a video camera attached to the microscope. The sections are first illuminated with polarized light, typically generated by a mercury lamp. The cells containing formazan crystals due to metabolically reduced tetrazolium salt brightly reflect polarized light. The images are analyzed by pixel image analysis, typically as described by Hoffman et al, *Proc. Natl. Acad. Sci. USA,* 86:2013–2017, (1989).

The slides are also analyzed for fluorescence using light passed through a filter providing the proper wavelength to activate the selected fluorescent dye. The number of bright pixels from the fluorescence or reflectance measurement is calculated using a modified Fas-Com version of the P-See program from The Microworks, Del Mar, Calif., typically run on an IBM PC XT type computer. Cell morphology can be observed due to the fluorescence whereby cancer cells can be distinguished from stromal cells. The slide images are digitized by a conventional digitizer board and the area of brightness corresponding to the number of labeled or bright cells is calculated as the area of enhanced pixels by the Fas-Com program. The area of enhanced pixels is proportional to the number of labeled cells. The ratio of formazan bright pixels to fluorescent dye bright pixels is calculated for each drug tested and compared to a control value to obtain the amount of drug-induced inhibition.

The sensitivity of the tumor to the drug can be determined by using the formula:

$$\text{Inhibition rate} = 100 - [(\text{PIAFC}_{Treated}/\text{PIAFD}_{Treated})/(\text{PIAF}_{Control}/\text{PIAFD}_{Control}) \times 100],$$

where PIAFC is pixel image analysis of formazan crystal reflection and PIAFD is pixel image analysis of fluorescent dye emissions.

In order to establish the accuracy of the presently claimed in vitro tests of the chemoactivity of the different drugs relative to the tumor tested, in vivo chemosensitivity tests were also performed, as described herein and show very high correlation to the in vitro drug response results.

Details of preferred embodiments of the method of this invention are provided in the following Examples. All parts and percentages are by weight unless otherwise indicated.

EXAMPLES I–IX

The method of this invention was performed with each of a plurality of drugs known to have varying effectiveness against various types of cancer. Drugs used were (I) mitomycin-C (about 100 ng/ml), (II) doxorubicin (about 29 ng/ml), (III) 5-fluorouracil (about 4 µg/ml), (IV) carmustine (about 0.2 µg/ml), (V) cisplatin (about 1.5 µg/ml), (VI) melphalan (about 1 µg/ml), (VII) vinblastine (about 7.3 ng/ml), (VIII) vincristine (about 23 ng/ml) and (IX) bleomycin (about 210 ng/ml), all from Sigma Chemical Co., (St. Louis, Mo.). The concentrations of these drugs represent approximately the levels achievable clinically and are termed "1X" concentrations. All were dissolved in physiological saline except for melphalan, which was dissolved in ethanol.

Human tumor specimens were derived from surgery. This tumor had been maintained by serial transplantation into nude mice. The specimen was minced aseptically into approximately 1-mm$^3$ pieces with a scalpel and forceps, and placed on collagen gels made from pigskin and available from Health Design Inc. (Rochester, N.Y.) or from Upjohn (Kalamazoo, Mich.). The sponge-gel supported tumors were cultured (histocultured) in six-well plates with about 2 ml of Eagle's minimum essential medium containing about 10% fetal bovine serum and about 1% nonessential amino acids, and about 0.1 mg/ml gentamicin sulfate (Gemini Bioproducts, Calabasas, Calif.) for about 24 hours. With the colon tissue, about 100 units/ml of penicillin G from Sigma was also added. The drugs indicated above were then added to the histoculture at the indicated concentration and maintained (incubated in histoculture) further to allow the drug to exert its antineoplastic effects, if any, on the histocultured sample.

A phosphate-buffered saline solution composed of about 138.7 mM NaCl, about 2.7 mM KCl, about 8 mM $Na_2HPO_4$, about 1.5 mM $KH_2PO_4$ was prepared. A quantity of 3-(4,5-Dimethyl- 2-thiazoyl)-2,5-diphenyl-2H-tetrazolium bromide (MTT) was dissolved in the phosphate-buffered saline to form a freshly prepared stock solution having about 8 mg/ml MTT. The solution was filtered through a 0.2-μm membrane filter from Millipore, (Bedford, Mass.).

The sponge-gel-supported tumor pieces, after about 24 hour incubation with the drugs, were transferred to drug free media and were incubated for about 2 hours at about 37° C. in a humidified sterile atmosphere, containing about 95% air and about 5% carbon dioxide with about 2 ml of a new solution composed of the MTT in the saline solution at a final concentration of about 0.4 mg/ml.

After about 2 hours, the gels were removed from the incubation media containing MTT and placed in about 2 ml of cold phosphate-buffered saline. The specimens were kept at about 4° C., and subsequently frozen whereupon 4-μm frozen sections were made. Water-soluble embedding media Tissue Tek OCT Compound from Baxter Labs (Irvine, Calif.) and a Tissue Tek II Cryostat, from Miles Laboratories, Inc. (Naperville, Ill.) were used in making the frozen sections.

The slides were then dipped for about 30 s in an about 1.25 μg/ml propidium iodide solution from Sigma, prepared in distilled water. After being dried, they were ready for pixel image analysis of formazan crystals (PIAFC) and pixel image analysis of fluorescent dye (PIAFD) measurements as described herein.

The image analysis system consisted of a Nikon Optiphot microscope connected to an RCA TC-1501 video camera, a Hitachi monitor and an IBM personal computer.

The measurements were conducted microscopically under a mercury lamp, using an IGS filter for polarized light and a DM 580 G-2A filter, composed of EX 510–560 excitation and BA 590 emission filters, for fluorescent light of the proper wavelength. The objective magnification was 200× and the image was digitized by a conventional digitizer board.

The areas of brightness corresponding to the amount of formazan crystals which reflect polarized light or to red nuclei due to fluorescence of the propidium iodide fluorescent dye were calculated as the ratio of the area of enhanced pixels to total pixels by the Image Scanner, Conway Filter and Bright Pixel Planimeter (DS-88 Digisector Video, Confil version 1.0 program from The Microworks, Del Mar, Calif.) running on an IBM PC-XT type computer.

The PIAFC and the PIAFD were measured in the non-drug-treated control twice, once at the beginning of the experiment and once at the end, within about 6 hours of the beginning. During this time there were no statistically significant changes detected, indicating that the system was stable during the measurement period.

The Figures illustrate the results of the method of this invention as exemplified in the above Examples.

Figure 2:
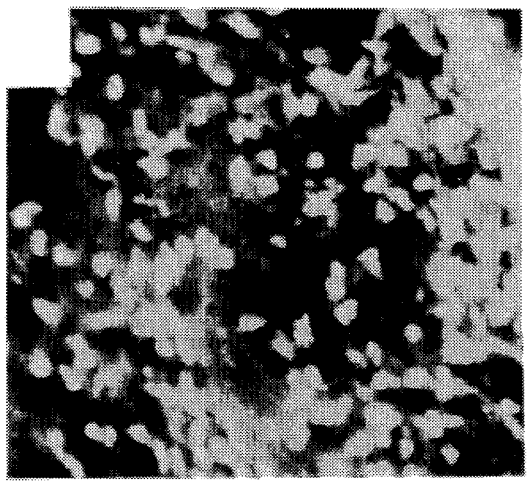
FIG. 2 is a photomicrograph of the sample of FIG. 1, under fluorescent light, showing dye fluorescence corresponding to the number of cell nuclei present.

FIG. 1 shows a frozen section of the colon tumor under polarized light after about 24 h culture in the presence of doxorubicin Example II) and about 1 h incubation with MTT. Formazan crystals present, due to the active metabolism of the living cells, are easily observed. The same field visualized under fluorescent light is seen in FIG. 2. The slide was stained with propidium iodide after the frozen section was made so that all cell membranes were opened and the total amount of nuclei can be visualized. By comparing FIG. 2 with FIG. 1 it is apparent that areas of high formazan crystal formation correspond to areas that contain nuclei. The absence of nuclei in some areas of the section corresponds to the absence of formazan crystals in those areas, thus demonstrating that MTT is being reduced only by cells and not by the drug used with this section. The inhibition rate formula given above can be used to demonstrate that the tumor is not sensitive in vitro to the drug doxorubicin (at 29 ng/ml) after the 24 h exposure.

Figure 3:
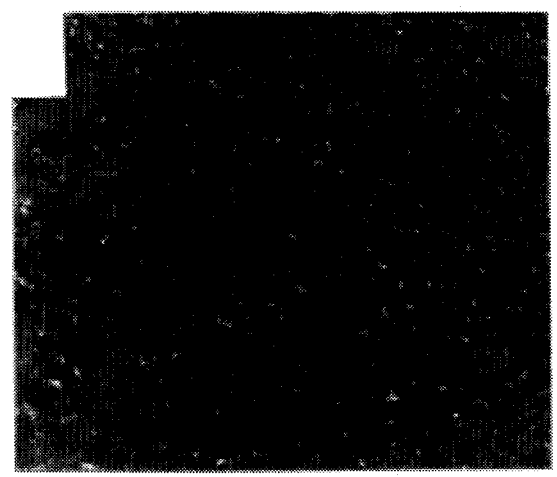
FIG. 3 is a photomicrograph of the sample under polarized light after incubation with an effective drug, showing the absence of formazan crystals.
Figure 4:
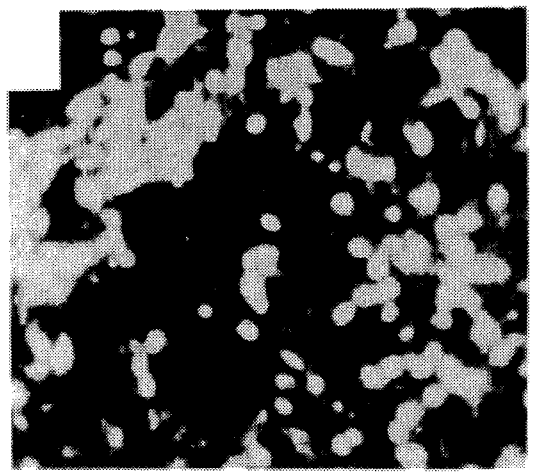
FIG. 4 is a photomicrograph of the sample of FIG. 3 under fluorescent light, showing dye fluorescence corresponding to the number of nuclei present.

FIG. 3 shows, under polarized light, a different frozen section of the same tumor incubated with a different drug, 1.5 μm/ml cisplatin (Example IV) for about 24 h. FIG. 4 shows the same field visualized under fluorescent light. In this case the PIAFC is very low with respect to PIAFD, so that their ratio divided by the control value (using the inhibition rate formula described above) is only 0.25%. Using that formula, the tumor is found to be 99.75% sensitive in vitro to the drug cisplatin.

Figure 5:
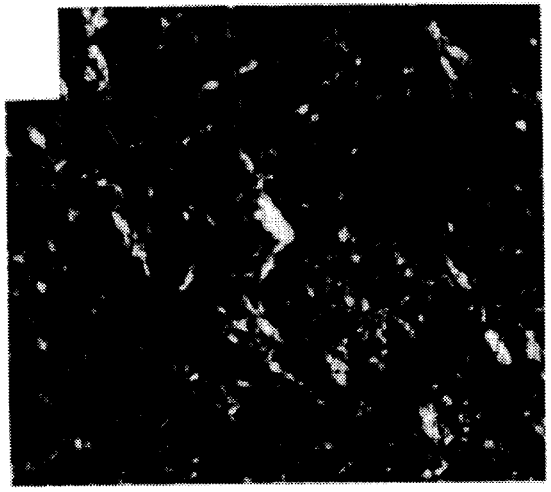
FIG. 5 is a photomicrograph of an untreated sample under polarized light, showing the appearance of the formazan crystals indicative of viable cells.
Figure 6:
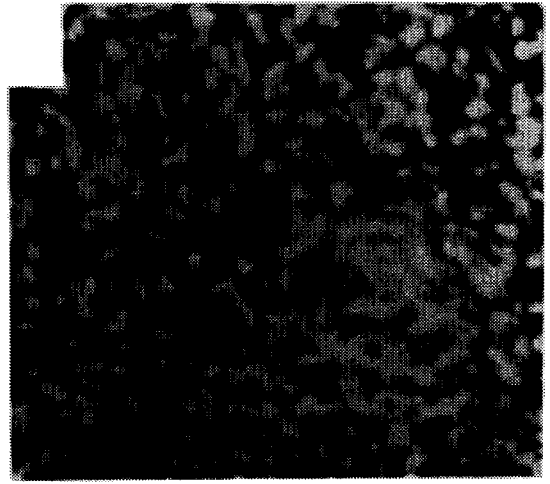
FIG. 6 is a photomicrograph of the untreated sample of FIG. 5 under fluorescent light, showing dye fluorescence corresponding to the number of nuclei present.

FIGS. 5 and 6 represent a piece of the tumor that has not been treated with a drug, as a control. FIG. 5 shows the untreated section visualized under polarized light while FIG. 6 shows that section under fluorescent light. In the control those areas showing the presence of large amounts of formazan crystals correspond to the areas having large numbers of nuclei, showing no diminution in the tumor cells.

Figure 7:
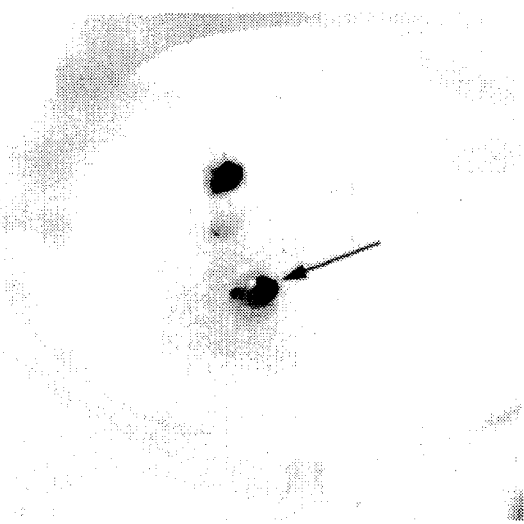
FIG. 7 is a photograph of a gel-supported tumor (arrow) in a six-well culture plate, treated with a drug, illustrating the heterogeneous behavior of a histocultured human tumor.

FIG. 7 illustrates the heterogeneous behavior of the tumor. The histocultured tumor was treated for about 24 hours with 100 ng/ml mitomycin-C (Example I), and a photograph of the entire histocultured tumor sample was taken in normal visible light.

Figure 8:
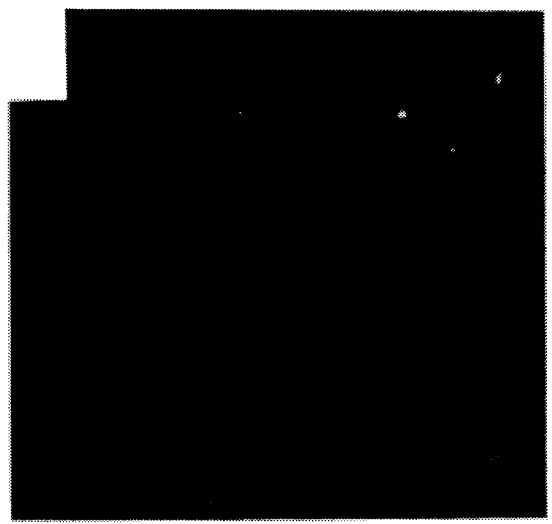
FIG. 8 is a photomicrograph of the sample of a portion of FIG. 7 under polarized light, showing absence of reduction of tetrazolium salt.
Figure 9:
FIG. 9 is a photomicrograph similar to FIG. 8, showing an area with active tetrazolium salt reduction.

FIGS. 8 and 9 show frozen sections from different regions of the tumor shown in FIG. 7, analyzed under polarized light with 170× magnification. FIG. 8 shows one area of the section where MTT reduction is absent while FIG. 9 shows another area of the section where MTT reduction is very active, demonstrating the wide variability of drug responsiveness within a single section.

Figure 10:
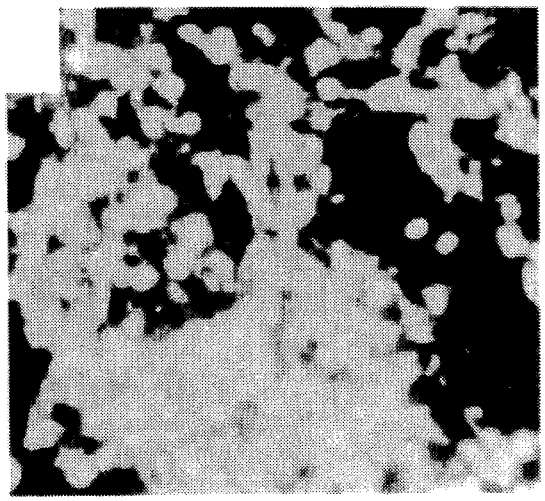
FIG. 10 is a photomicrograph of the area of FIG. 8 under fluorescent light.
Figure 11:
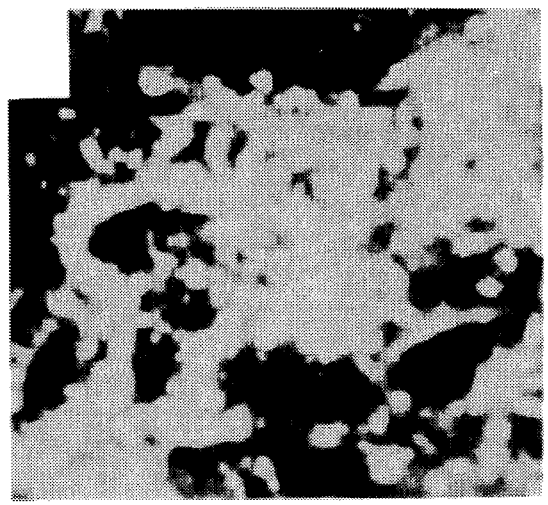
FIG. 11 is a photomicrograph of the area of FIG. 9, under fluorescent light.

FIGS. 10 and 11 show the sections of FIGS. 8 and 9, respectively, but analyzed under fluorescent light. The total number of nuclei are shown to be about the same in both areas, which is confirmed by PIAFD. The PIAFC/PIAFD ratio, measured in the areas shown in FIG. 9 where formazan crystals were observed, was very similar to that obtained with the control value using the drug inhibition formula described above. Thus, using the inhibition formula, the tumor showed only an 18% sensitivity in vitro, indicating resistance of the tumor to the drug mitomycin-C.

Figure 12:
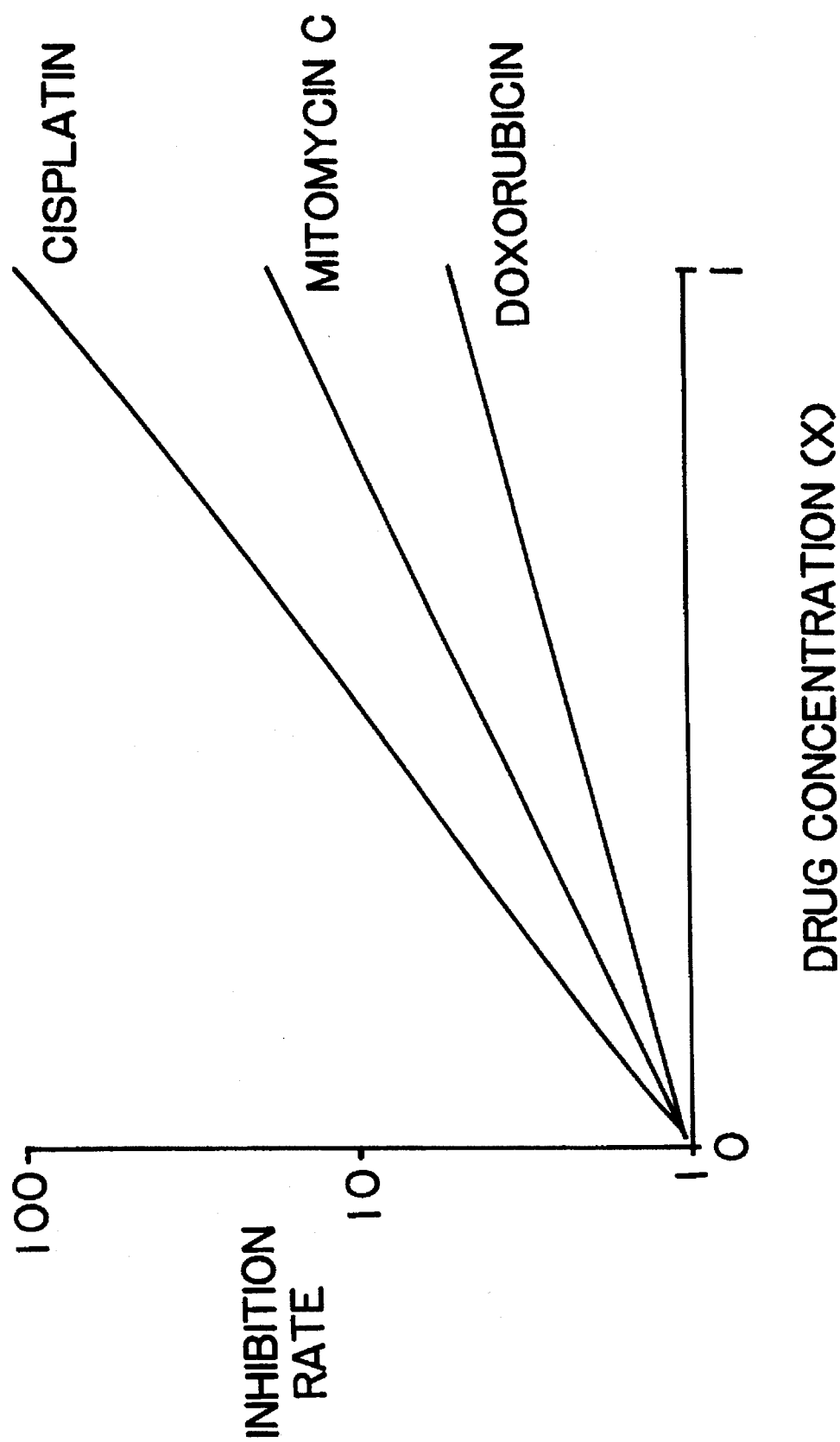
FIG. 12 is a graphical representation showing the relative tumor inhibitions rates for the drugs of FIGS. 1, 3 and 9.

FIG. 12 graphically summarizes the results of the assays performed above with respect to cisplatin, mitomycin-C and doxorubicin. Of these, cisplatin is found to be most effective, while doxorubicin is found to have a low inhibition rate.

EXAMPLE X

In order to correlate the relative effectiveness of drugs shown by the in vitro method described above and in vivo use of the same drugs, comparative in vivo tests upon human tumor xenografts in nude mice were performed. Tumors evaluated were the gastric cancers St-4, St-15, St- 40, H- 111 and SC-2-JCK; the colon cancers Co-3, Co-4 (used in Examples I–IX, above), Co-6 and Co-8; the breast cancers MX- 1 and MCF-7; the small-lung cancers Lu-24, Lu-130 and H-69; hepatoma Li-7 and neuroblastoma CR-N89.

Drugs used were mitomycin C (MMC), doxorubicin (DOX), cisplatinum (DDP), 5-fluorouracil (5FU), and cyclophosphamide (CCPM). Melphalan (MEL) was used as a substitute for cyclophosphamide during the in vitro tests. The drugs, obtained from Sigma, were dissolved in physiological saline, except for melphalan which was dissolved in ethanol.

Histocultures were prepared as described herein. Tumors were explanted using the sponge-gel-supported three-dimensional in vitro histoculture system described by Hoffman et al., *Proc. Natl. Acad. Sci. USA*, 83:2694–2698,1986. Collagen gels manufactured from pig skin (Health Design) were removed from their sterile packages and cut with scissors into 1 $Cm^2$ pieces and placed in 6-well plates.

To that end, tumors in the exponential growth phase in nude mice were resected aseptically, necrotic tissues were cut away and the remaining healthy tumor tissues were minced with scissors into 2-mm diameter bits in Hanks' balanced salt solution and further minced into 4-to-10 1-mm diameter bits, which were placed on the same collagen surface.

Two ml/well of Eagle's minimum essential medium containing about 10% serum were added into the 6-well plates, at which volume the upper part of the gels were reached but not covered. The histocultures were then incubated for a total of about 1–2 days at about 37° C. in a humidified atmosphere containing about 95% air with the balance carbon dioxide. Thereafter, a drug for efficacy (drug-response) evaluation was added to the histoculture medium and the culture maintained for about 24 hours. At least four concentrations were tested for each drug in any single assay. All drug concentrations were tested in triplicate wells. Drugs tested were mitomycin C, doxorubicin, 5-fluorouracil, cisplatinum and melphalan at a concentration of 100 ng/ml, 29 ng/ml, 4 ug/ml, 1.5 ug/ml and 1 ug/ml, respectively, dissolved in PBS, except for melphalan which was dissolved in ethanol. After exposure to the drug, the drug was removed from the histoculture by changing the culture medium.

An in vitro MTT assay was then performed as described herein to evaluate the activity of living cells in and on the collagen gels. MTT stock solution, prepared by dissolving the powder at about 8 mg/ml in phosphate-buffered saline and filtered through a 0.45 μm membrane filter from Millipore was added to each well to produce a final concentration of about 0.4 mg/ml, and the plates were further incubated for about 1–3 hours. Thereafter, the histocultured tissue sample was placed in cold PBS and kept at 4° C. until 4μ frozen sections were made using water-soluble embedding media. The resulting slides were then dipped in about 1.25 μg/ml propidium iodide (PI) for about 2 minutes and when dried, were evaluated by pixel image analysis of the formazan crystals (PIAFC) and the PI-stained nuclei (PIAFD) as before.

For image analysis a Nikon Optiphot microscope with an RCA video camera was used. The image was digitized by a conventional digitizer board and the area of brightness corresponding to the number of labeled or bright cells was calculated as the area of enhanced pixels by the modified Fas-Com program. The area of enhanced pixels is proportional to the number of labeled cells. Slides were viewed under both bright-field light as well as polarizing light without bright-field. The cells containing formazan crystals due to MTT reduction brightly reflect the polarized light generated by a mercury lamp. The slides were also analyzed for PI fluorescence whereby the dye was activated using a DM-580 G2A filter. The number of bright pixels from PI fluorescence and the number of bright pixels from formazan reflectance were calculated by a modified version of the Fas-Com version of the P-See program (The Microworks), run on an IBM PC XT type computer. Cell morphology could be observed due to PI fluorescence whereby cancer cells could be distinguished from stromal cells. The ratio of formazan bright pixels to PI bright pixels was calculated for each drug concentration tested and compared to the control value in order to obtain the amount of drug-induced inhibition.

Tumor fragments, approximately 3×3×3 mm in size, were also inoculated into the Subcutaneous tissue of either side of the backs of BALB/c nude mice (6 to 8 weeks old, weighing 20–22 gms) to determine the in vivo responsiveness of the xenograft tumors to various drugs. The length and width of the tumors were measured with sliding calipers three times a week by the same person. The xenograft tumor weight was calculated using the formula: Tumor weight (mg)=length (mm)×[width $(mm)]^2/2$. When the tumors reached about 100– 300 mg, usually 2–3 weeks after the tumor inoculations, tumor-bearing mice were randomized into control and treated groups, consisting of at least four mice each, and treatment was initiated. Each of the drugs was dissolved in 0.2 ml of 0.9% NaCl per 20 g of body weight. The drugs of mitomycin C, cisplatinum, doxorubicin, 5-fluorouracil and cyclophosphamide were administered at dosages of 3, 9, 4, 50 and 80 mg/kg, respectively, which had been determined to be the maximum tolerated doses for nude mice, as described by Kubota et al, *Jpn. J. Cancer. Res. (Gang)*, 77:502–507, 1986. All the drugs were administered bolus i.p. except for doxorubicin which was given i.v. Mice and tumors were observed 3 times a week for 3 weeks after the initial treatment and the relative mean tumor weight (RW) was calculated as the ratio $W_t/W_o$, where $W_o$ is mean tumor weight at the initiation of treatment and $W_t$ is the tumor weight at the time of measurement. The anticancer effects of the drugs were evaluated in terms of the lowest ratio of mean tumor weight of the treated tumors to the mean tumor weight of the control group tumors. The antitumor activity was evaluated as positive (i.e., sensitive) when the lowest ratio of relative mean tumor weight of the treated group to the relative mean tumor weight of the control group was less than about 42%, which is equivalent to about 25% reduction of each diameter.

FIG. 13 summarizes the results obtained from the comparison between the in vitro non-colorimetric MTT end point and in vivo results. The calculations shown were made as follows: true positive is the number of cases measured as sensitive both in vitro and in vivo; true negative is the number of cases measured as resistant both in vitro and in vivo; false positive is the number of cases measured sensitive in vitro and resistant in vivo; false negative is the number of cases measured resistant in vitro and sensitive in vivo; accuracy is the percent accuracy of the MTT assay calculated as [(number of true positives plus true negatives)/total]×100; specificity is the percent specificity calculated as [number of true negatives/(number of true negatives plus false positives)]×100; predictive value positive (predict.pos.val.) is calculated as [number of true positives/(number of true positives plus false positives)]×100; and predictive value negative (predict.neg.val.) is calculated as [number of true negatives/(number of true negatives plus false negatives)]×100.

The results summarized in FIG. 13 indicate a total specificity of about 93.8% and a total accuracy of about 74.6% of the new MTT end point in histoculture with nine different human xenograft tumors grown in nude mice with respect to the in vivo data. This allows prediction of positive and negative responses to drugs, with a rate of about 70% and about 71.8%, respectively. The histoculture method with the MTT end point measured by pixel analysis allows the simultaneous observation of the histology of human tumor specimens in vitro and gives a relatively high correlation with in vivo drug response and resistance.

EXAMPLES XI–XV

The method of Examples I–IX is repeated, except that the following tetrazolium salts are used in place of MTT: (XI) 2,2',5,5'-Tetra-p-nitrophenyl-3,3'-[3,3'-dimethoxy- 4,4'-diphenylene]ditetrazolium chloride (TNBT), (XII) 3,3'-[ 3,3'-Dimethoxy(1,1'-bi-phenyl)-4,4'-diyl]-bis[2,5-diphenyl-2H-tetrazolium] dichloride (tetrazolium blue; TB), (XIII) 2,3,5-Triphenyltetrazolium chloride (tetrazolium red; TR), (XIV) 2,5-Diphenyl-3-[α-naphthyl]-tetrazolium chloride (tetrazolium violet; TV), (XV) 2-[4-Iodophenyl]-3-[4-nitrophenyl] -5-phenyltetrazolium chloride (INT), (XVI) 2,2',5, 5'-Tetraphenyl-3,3'-[p-diphenylene]ditetrazolium chloride, (XVII) 2,2'-Di-p-nitro-phenyl-5,5'-diphenyl-3,3'-[ 3,3'-dimethoxy-4,4'-diphenylene]ditretrazolium chloride (NBT), and (XVIII) 2,2'-Di[p-nitro-phenyl]-5,5'-di[p-thiocarbamylphenyl] -3,3'-[3,3'-dimethoxy-4,4'-biphenylene] ditretrazolium chloride (TC-NBT). In each case, an excellent correlation between in vitro and in vivo drug response characteristics is obtained.

Other applications, variations and ramifications of this invention will occur to those skilled in the art upon reading this disclosure. Those are intended to be included within the scope of this invention, as defined in the appended claims.

What is claimed is:

1. A method of evaluating the effectiveness of drugs in inhibiting the growth of tumor cells which comprises the steps of:

providing a sample of a tumor;

histoculturing said sample on a support matrix;

adding a selected quantity of a drug to be evaluated to said histocultured sample;

histoculturing said sample with said added drug;

removing said added drug from said histocultured sample;

adding a selected quantity of a tetrazolium salt to said histocultured sample;

histoculturing said sample with said added tetrazolium salt;

removing said added tetrazolium salt from said histocultured sample;

preparing a frozen section of said sample;

staining said section with a fluorescent dye;

exposing said section to polarized light and measuring a first light reflected by said section which is proportional to the number of living cells in the sample;

exposing said section to light of wavelengths to which said dye responds and measuring a second fluorescent light emitted by said section which is proportional to the total number of cells present in the sample; and comparing the relative amounts of said first and second light measurements;

whereby the effectiveness of said drug tested is determined by calculating the ratio of said first light to said second light and comparing said ratio to a control value to obtain the amount of drug-induced inhibition.

2. The method according to claim 1 wherein said first light and said second light are each evaluated by pixel analysis.

3. The method according to claim 1 wherein said tumor sample is in the form of approximately cubical pieces having volumes of from about 0.5 to 1.0 mm$^3$.

4. The method according to claim 3 wherein said tumor pieces are cultured on collagen gels made from pigskin.

5. The method according to claim 1 wherein said samples are histocultured prior to application of said drug for from about 1 to 4 days.

6. The method according to claim 1 wherein said tetrazolium salt is selected from the group consisting of 3-[ 4,5-Dimethylthiazol-2-yl]-2,5-diphenyltetrazolium bromide; 2,2',5,5'-Tetra-p-nitrophenyl-3,3'-[3,3'-dimethoxy-4, 4'-diphenylene] ditetrazolium chloride; 3,3'-[3,3'-Dimethoxy( 1,1'-bi-phenyl)-4,4'-diyl]-bis[2,5-diphenyl-2H-tetrazolium] dichloride; 2,3,5-Triphenyltetrazolium chloride; 2,5-Diphenyl-3-[α-naphthyl]-tetrazolium chloride; 2-[4-Iodophenyl]-3-[4-nitrophenyl]-5-phenyltetrazolium chloride; 2,2',5,5'-Tetraphenyl-3,3'-[p-diphenylene] ditetrazolium chloride; 2,2'-Di-p-nitro-phenyl- 5,5'-diphenyl-3,3'-[3,3'-dimethoxy-4,4'-diphenylene] ditretrazolium chloride; 2,2'-Di[p-nitrophenyl] -5,5'-di[p-thiocarbamylphenyl]-3,3'-[3,3'-dimethoxy- 4,4'-biphenylene]ditretrazolium chloride, and mixtures thereof.

7. The method according to claim 1 wherein said tetrazolium salt is3-(4,5-Dimethylthiazol-2-yl)-2,5-diphenyltetrazolium bromide.

8. The method according to claim 1 wherein said fluorescent dye is propidium iodide.

9. The method according to claim 1 wherein the steps of claim 1 are repeated a plurality of times, using different concentrations of said drug, whereby the optimum drug concentration for inhibiting the growth of tumor cells is determined.

10. The method according to claim 1 wherein said sample of tumor is incubated for at least 1 hour between the addition of said tetrazolium salt and preparation of said frozen section.

11. The method according to claim 1 wherein different areas of said section exposed to said polarized and said wavelengths of light are compared, whereby the heterogeneity of the section can be evaluated.

12. A method of measuring the relative effectiveness of selected drugs in inhibiting growth of tumor cells which comprises the steps of:

providing first and second samples of histocultured tumors;

adding a selected amount of a drug to said first sample;

histoculturing said first and second samples;

removing said added drug from said first sample;

adding a selected quantity of a tetrazolium salt to said first and second samples;

histoculturing said samples with said added tetrazolium salt;

removing said added tetrazolium salt from said samples;

preparing a frozen section of each sample;

staining each section with a fluorescent dye;

exposing each section to polarized light and measuring the polarized light reflected by each sample;

exposing each section to light of wavelengths to which said dye responds and measuring the fluorescent light emitted by each of said samples; and comparing the results of said light measurements;

whereby the relative effectiveness of said drug is determined by calculating a first ratio of said first light to said second light of said first sample and a second ratio of said first light to said second light of said second sample and comparing said first and second ratios.

13. The method according to claim 12 wherein said reflected light resulting from polarized light exposure and said emitted fluorescent light resulting from said wavelengths of light exposure are each evaluated by pixel analysis.

14. The method according to claim 12 wherein said tumor samples are in the form of approximately cubical pieces having volumes of from about 0.5 to 1.0 mm$^3$.

15. The method according to claim 14 wherein said tumor pieces are cultured on collagen gels made from pigskin.

16. The method according to claim 12 wherein said samples are incubated prior to application of said drug for from about 1 to 4 days.

17. The method according to claim 12 wherein said tetrazolium salt is selected from the group consisting of 3-[4,5-Dimethylthiazol-2-yl]-2,5-diphenyltetrazolium bromide; 2,2',5,5'-Tetra-p-nitrophenyl-3,3'-[3,3'-dimethoxy-4,4'-diphenylene] ditetrazolium chloride; 3,3'-[3,3'-Dimethoxy( 1,1'-bi-phenyl)-4,4'-diyl]-bis[2,5-diphenyl-2H-tetrazolium] dichloride; 2,3,5-Triphenyltetrazolium chloride; 2,5-Diphenyl-3-[α-naphthyl]-tetrazolium chloride; 2-[4-Iodophenyl]-3-[4-nitrophenyl]-5-phenyltetrazolium chloride; 2,2',5,5'-Tetraphenyl-3,3'-[p-diphenylene] ditetrazolium chloride; 2,2'-Di-p-nitro-phenyl- 5,5'-diphenyl-3,3'-[3,3'-dimethoxy-4,4'-diphenylene] ditetrazolium chloride; 2,2'-Di[p-nitrophenyl] -5,5'-di[p-thiocarbamylphenyl]-3,3'-[3,3'-dimethoxy- 4,4'-biphenylene]ditetrazolium chloride, and mixtures thereof.

18. The method according to claim 12 wherein said tetrazolium salt is 3-(4,5-Dimethylthiazol-2-yl)-2,5-diphenyltetrazolium bromide.

19. The method according to claim 12 wherein said fluorescent dye is propidium iodide.

20. The method according to claim 12 wherein the steps are repeated a plurality of times, using different concentrations of said drug, whereby the optimum drug concentration for inhibiting the growth of tumor cells is determined.

21. The method according to claim 12 wherein said samples are incubated for at least 1 hour between the addition of said tetrazolium salt and preparation of said frozen section.

22. The method according to claim 12 wherein different areas of said section exposed to said polarized and said wavelengths of light are compared, whereby the heterogeneity of the section can be evaluated.

23. The method according to claim 12 wherein selected amounts of additional drugs are added to additional tumor samples and said method is performed on all samples, whereby the relative effectiveness of different drugs with respect to the tumor is determined.

24. The method according to claim 12 wherein said comparison is accomplished by pixel analysis using the formula:

$$\text{Inhibition rate} = 100 - [(PIAFC_{Treated}/PIAFD_{Treated})/(PIAFC_{control}/PIAFD_{control}) \times 100],$$

where PIAFC is pixel image analysis of formazan crystal reflection and PIAFD is pixel image analysis of fluorescent dye emissions.

* * * * *